(12) United States Patent
Boock et al.

(10) Patent No.: US 8,267,981 B2
(45) Date of Patent: Sep. 18, 2012

(54) SUTURE ANCHOR WITH IMPROVED DRIVE HEAD

(75) Inventors: Robert Boock, Braintree, MA (US); Nathan Cauldwell, Attleboro, MA (US)

(73) Assignee: DePuy Mitek, Inc., Raynham, MA (US)

( * ) Notice: Subject to any disclaimer, the term of this patent is extended or adjusted under 35 U.S.C. 154(b) by 2153 days.

(21) Appl. No.: 10/458,482

(22) Filed: Jun. 10, 2003

(65) Prior Publication Data

US 2004/0254580 A1 Dec. 16, 2004

(51) Int. Cl.
*A61B 17/04* (2006.01)
*A61B 17/86* (2006.01)
*A61F 2/08* (2006.01)

(52) U.S. Cl. .......................... 606/308; 606/232

(58) Field of Classification Search ............... 606/72, 606/73, 74, 75, 232, 308, 310
See application file for complete search history.

(56) References Cited

U.S. PATENT DOCUMENTS

| | | | |
|---|---|---|---|
| 3,134,292 A | 5/1964 | Walton | |
| 4,632,100 A | 12/1986 | Somers et al. | |
| 5,401,133 A | 3/1995 | Kuchler | |
| 5,618,314 A | 4/1997 | Harwin et al. | |
| 5,690,676 A | 11/1997 | DiPoto et al. | |
| 5,752,963 A | 5/1998 | Allard et al. | |
| 5,814,051 A | 9/1998 | Wenstrom, Jr. | |
| 5,964,783 A | 10/1999 | Grafton et al. | |
| 6,045,573 A * | 4/2000 | Wenstrom et al. | 606/232 |
| 6,149,653 A * | 11/2000 | Deslauriers | 606/72 |
| 6,511,499 B2 | 1/2003 | Schmieding et al. | |
| 6,517,564 B1 * | 2/2003 | Grafton et al. | 606/213 |
| 6,799,480 B1 * | 10/2004 | Walsh et al. | 73/862.21 |
| 7,055,415 B1 * | 6/2006 | Walsh et al. | 81/477 |
| 2001/0037131 A1 | 11/2001 | Schmieding et al. | |
| 2002/0052605 A1 | 5/2002 | Grooms et al. | |
| 2002/0173822 A1 | 11/2002 | Justin et al. | |

FOREIGN PATENT DOCUMENTS

| | | |
|---|---|---|
| EP | 0 791 331 A | 8/1997 |
| GB | 13753 | 0/1898 |
| JP | 08019555 A | 1/1996 |
| JP | 9-510116 T | 10/1997 |
| JP | 2003010198 A | 1/2003 |
| WO | WO 03/072962 A | 9/2003 |

OTHER PUBLICATIONS http://myword.info/sendword.php?oval_head_1-a. definition of Oval Head.*
http://myword.info/sendword.php?oval_head 1-a. definition of Oval Head Oct. 12, 2006.*
Japanese Office Action, for Japanese Patent Application No. 2004-171469, dated May 18, 2010.
Japanese Office Action, for Japanese Patent Application No. 2004-171469, dated Sep. 7, 2010 and English Translation.

* cited by examiner

*Primary Examiner* — Thomas J Sweet

(57) ABSTRACT

A suture anchor is provided including an elongate shank defining a longitudinal axis and having at least one bone-engaging thread formed thereon, and a drive head having a proximal end and a distal end mated to the elongate shank. The drive head has a substantially oval shape and includes at least one suture attachment member formed in a portion of the drive head. The configuration of the drive head is particularly advantages in that it provides a suture anchor having improved physical properties, including a high failure torque and a high stripping strength.

14 Claims, 7 Drawing Sheets

SUTURE ANCHOR WITH IMPROVED DRIVE HEAD

FIELD OF THE INVENTION

The present invention relates to suture anchors having improved physical properties, and in particular to suture anchors having a high failure torque.

BACKGROUND OF THE INVENTION

Suture anchors are often used to attach a length of suture to bone in order to use the suture to secure detached soft tissue to the bone. Suture anchors typically have an anchor body, a suture attachment feature, and a bone engaging feature for retaining the suture anchor within bone. The anchor can be inserted into a preformed hole in the bone, and/or the anchor can be self-tapping and thus can include threads for mating the anchor within bone. Most suture anchors require the use of an insertion tool for driving the suture anchor into bone. Such insertion tools are typically formed from an elongate shank having a mating feature formed on a distal end thereof for mating with a corresponding mating feature formed on or in the head of a suture anchor. One common type of driver tool includes a hex-shaped or square-shaped socket for receiving a corresponding hex-shaped or square-shaped head of a suture anchor.

While conventional suture anchors and suture anchor drivers are sufficient, they have some drawbacks. Hex-shaped and square-shaped anchor heads, for example, tend to have a relatively low stripping strength. This can be due to the structural integrity of the anchor head, which is sometimes weakened by the attachment feature used to attach a suture to the anchor head. If the attachment feature decreases the amount of material on the anchor head that interfaces with the driver, then the amount of material that needs to be removed or "stripped" from the drive head is reduced, thus reducing the stripping strength of the head.

Conventional suture anchor heads also tend to have a relatively low failure torque, which can result in shearing of the head during insertion. This type of failure can also be caused by the location of the suture attachment feature on the anchor head, which can reduce the overall cross-sectional area of the drive head. The Bio-corkscrew™ anchor, manufactured by Arthrex Inc., of Naples, Fla., is one example of a suture anchor having a suture attachment feature that can interfere with the structural integrity of the anchor. In particular, a loop is molded into and embedded within the anchor such that the loop extends outward from the head of the anchor to receive a suture. As a result of the placement of the looped suture through the anchor, the entire anchor head is relatively weak and thus has the potential to shear off during insertion.

One option to increase the failure torque of an anchor head is to increase the size of the head. Large anchor heads, however, require a large driver tool, which in turn requires a relatively large bone tunnel to be formed in the bone. This is particularly undesirable, especially where the bone tunnel is to be formed in the cancellous bone. Accordingly, most suture anchors are adapted to for use with a relatively small driver tool, and thus they have a relatively small drive head which can result in a low failure torque and a low stripping strength.

Accordingly, there remains a need for suture anchors having improved physical properties, and in particular having a high failure torque and a high stripping strength.

SUMMARY OF THE INVENTION

The present invention generally provides a suture anchor including an elongate shank defining a longitudinal axis and having at least one bone-engaging thread formed thereon, and a drive head having a proximal end and a distal end mated to the elongate shank. The drive head has a substantially oval shape and at least one suture attachment member formed in a portion of the drive head. The configuration of the drive head is particularly advantageous in that it provides a suture anchor having improved physical properties, including a high failure torque and a high stripping strength. In an exemplary embodiment, the drive head has a failure torque of at least about 5.0 inch pounds, and the drive head has a tensile strength of at least about 60 pounds force (lbf).

In one embodiment, the suture attachment member comprises at least one suture tunnel extending through the drive head, either substantially transversely or such that the suture tunnel(s) intersects the longitudinal axis of the suture anchor. The suture attachment member can also include a longitudinally oriented suture-receiving channel formed on an outer surface of the drive head and originating at and extending proximally from each opening of the at least one suture tunnel. In an exemplary embodiment, the suture tunnel(s) are formed proximal to the distal end of the drive head to present a channel-free portion in the drive head. The channel-free portion provides additional structural integrity to the drive head of the suture anchor to minimize the risk of shearing during insertion. In another exemplary embodiment, the drive head includes a first suture tunnel having a first pair of opposed suture-receiving channels extending proximally therefrom, and a second suture tunnel having a second pair of opposed suture-receiving channels extending proximally therefrom.

In other aspects, a suture anchor and installation kit is provided including at least one suture anchor and a cylindrical driver tool. The suture anchor has a shank with bone-engaging threads formed thereon and defining a longitudinal axis. A drive head is formed on the shank and has an oval shape with at least one longitudinally oriented suture-receiving channel formed therein. The cylindrical driver tool has a distal end with a socket formed therein having an oval shape adapted to receive and engage the drive head of the suture anchor. In an exemplary embodiment, the driver tool has an outer diameter that is equal to or less than an outer-most diameter of the suture anchor.

Methods for using a suture anchor in accordance with the present invention are also provided.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1A:
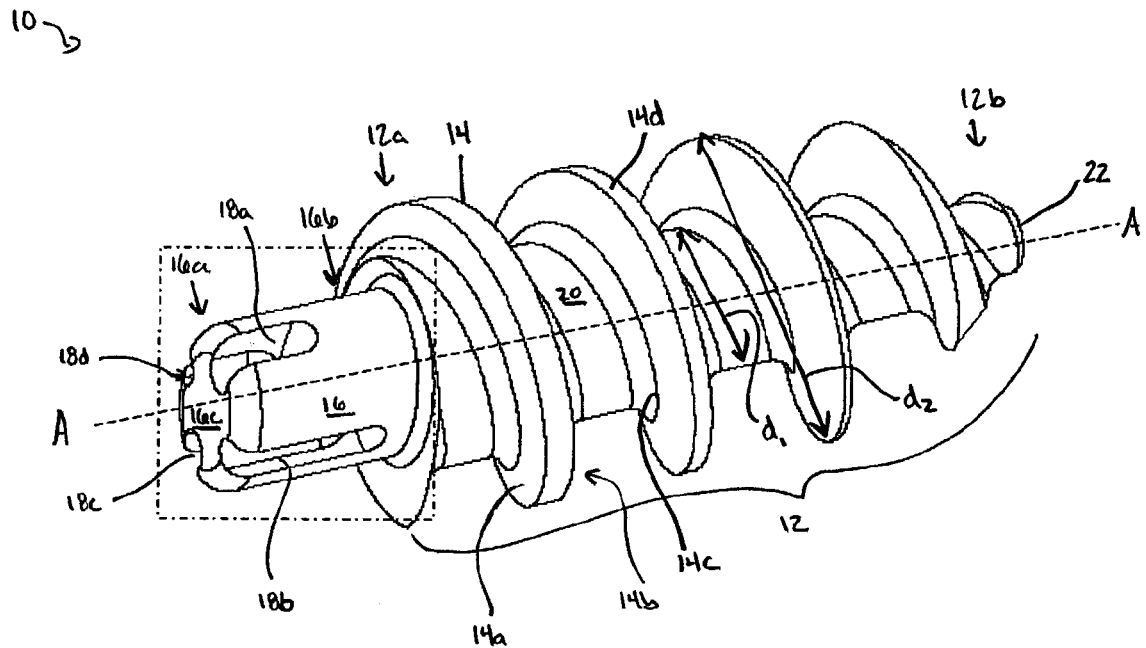
FIG. 1A is a perspective view of a suture anchor according to one embodiment of the present invention.
Figure 1B:
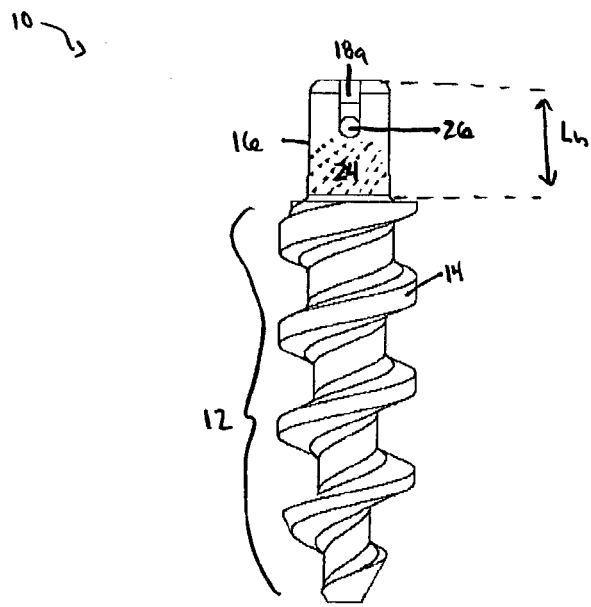
FIG. 1B is another perspective view of the suture anchor shown in FIG. 1A.

As shown in FIGS. 1A and 1B, the present invention generally provides a suture anchor 10 including an elongate shank 12 defining a longitudinal axis A and having at least one bone-engaging thread 14 formed thereon, and a drive head 16 having a proximal end 16a and a distal end 16b mated to the elongate shank 12. The drive head 16 has a substantially oval shape and includes at least one suture attachment member formed therein. The configuration of the drive head 16 is particularly advantages in that it provides a suture anchor 10 having improved physical properties, including a high failure torque and a high stripping strength.

The elongate shank 12 of the suture anchor 10 can have a variety of configurations, and can include a variety of different bone-engaging features formed thereon. FIGS. 1A and 1B illustrate an exemplary embodiment of a bone anchor 10 having a shank 12 including a core 20 with a single helical thread 14 extending around the core 20 from a proximal end 12a to a distal end 12b of the shank 12. The thread 14 includes proximal and distal facing flanks 14a, 14b that extend between a root 14c and a substantially flattened crest 14d. The thread 14 defines a major diameter $d_2$ of the shank 12, which can vary along the length of the shank 12, but the major diameter $d_2$ is preferably substantially constant along a substantial portion of the shank 12. The threads 14, however, can taper at the distal portion of the shank 12 to terminate at an apex 22 which forms the distal tip of the shank 12. The core 20 of the shank 12 defines a minor diameter $d_1$ that can also be substantially constant or can vary along the length of the shank 12. As shown in FIG. 1A, the core 20 tapers from a proximal end 12a to a distal end 12b. A person skilled in the art will appreciate that the shank 12 shown in FIG. 1A is merely an exemplary embodiment of a shank 12, and that a variety of different shanks having different bone-engaging features can be used with a suture anchor 10 in accordance with the present invention.

Figure 1C:
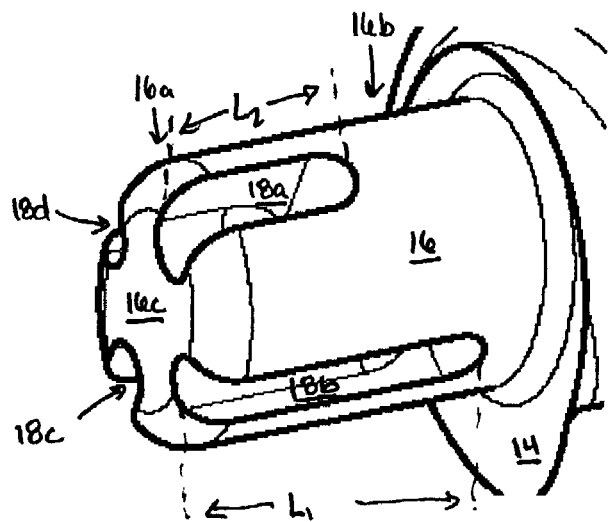
FIG. 1C is an enlarged, perspective view of the drive head portion of the suture anchor shown in FIG. 1A.
Figure 1D:
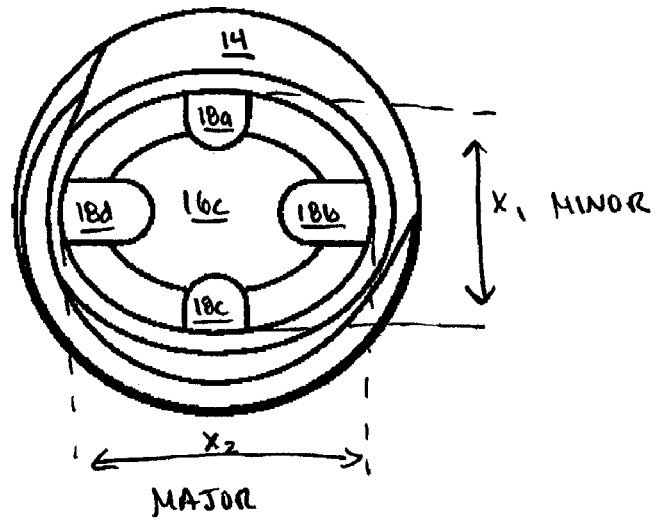
FIG. 1D is top view of the suture anchor shown in FIG. 1A.

The head 16 of the suture anchor 10 is shown in more detail in FIGS. 1C and 1D, and is attached to, or more preferably is formed integrally with, the shank 12. The head 16 has a generally oval shape defining a minor diameter $x_1$ and a major diameter $x_2$. In an exemplary embodiment, the minor diameter $x_1$ of the head 16 is about three-fourths (¾) the size of the major diameter $x_2$ of the head, and the major diameter $x_2$ of the head 16 is equal to or less than the minor diameter $d_1$ of the shank 12. The relatively small size of the major diameter $x_2$ of the head 16 as compared to the minor diameter $d_1$ of the shank 12 is particularly desirable so that the head 16 will not require a larger bone tunnel to be formed in the bone than is necessary. The head 16 further includes a length $L_h$ (shown in FIG. 1B) that extends between the proximal and distal ends 16a, 16b thereof. The length $L_h$ of the head 16 can vary, but preferably the length $L_h$ of the head 16 is optimized to allow the head to be received within a driver tool and to be driven into bone without shearing off.

Figure 1E:
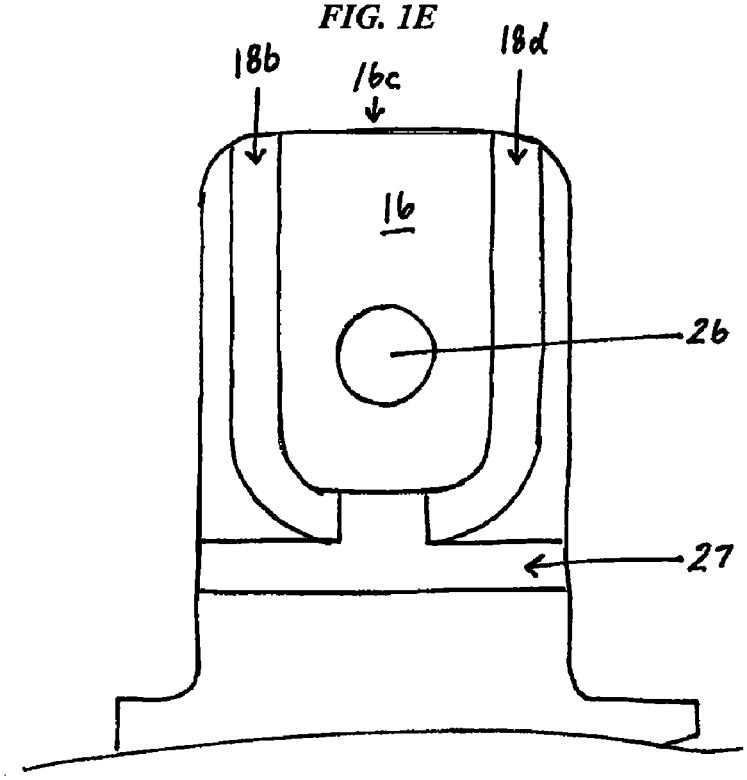
FIG. 1E is a cross-sectional view of the suture anchor shown in FIG. 1A.
Figure 1F:
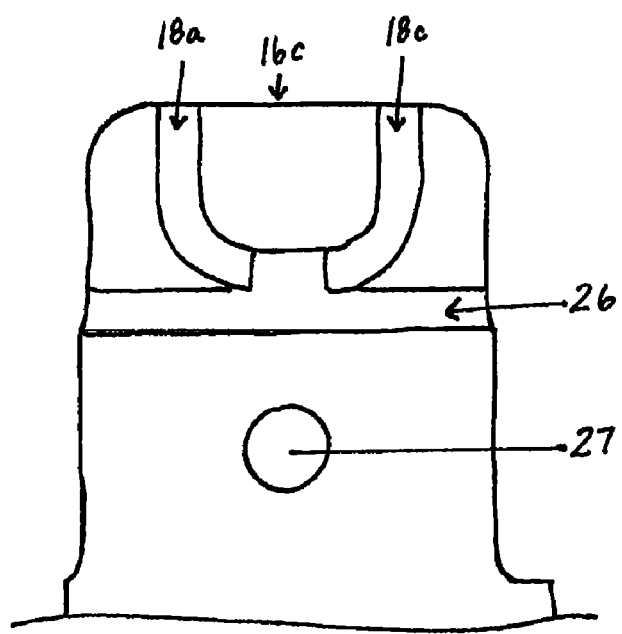
FIG. 1F is a cross-section view of the suture anchor shown in FIG. 1A.

The head 16 of the suture anchor 10 further includes at least one suture attachment member formed thereon or therein for receiving one or more sutures. While a variety of suture attachment members can be used, FIGS. 1A–1F illustrate an exemplary embodiment of the suture anchor 10 having first and second suture tunnels 26, 27 that extend through the head and that allow a length of suture to be disposed therethrough. The first and second suture tunnels 26, 27 can extend at virtually any orientation though the anchor head, but as shown in FIGS. 1A, 1E and 1F they preferably extend transversely through the anchor head 16 at different positions along the longitudinal axis A of the anchor 10 to prevent the tunnels from intersecting, so as to preserve the structural integrity of the head 16. In an exemplary embodiment, the suture tunnels terminate at a position proximal to the distal end 16b of the drive head 16 to provide a channel-free portion 24 (shown in FIG. 1B) in the head 16. Since the distal portion of the anchor head 16 is typically the part of the anchor 10 that is under the most stress during insertion, the channel-free portion 24 provides a much stronger, more dense portion of the anchor head 16 that will minimize the risk of shearing during insertion.

The suture anchor 10 can also optionally include four longitudinally oriented suture-receiving grooves or channels 18a, 18b, 18c, 18d formed therein. The suture-receiving channels 18a, 18b, 18c, 18d are formed in the outer surface of the head 16 and are preferably spaced equidistant from one another. As shown in FIG. 1D, two opposed suture-receiving channels 18d, 18b are positioned along the major diameter $x_2$ of the anchor head 16, and the other two opposed suture-receiving channels 18a, 18c are positioned along the minor diameter $x_2$ of the head 16. The position of the suture-receiving channels 18a, 18b, 18c, 18d can also vary, but preferably they extend through the proximal surface 16c of the drive head 16 and terminate at an opening of the corresponding suture tunnel. Where the suture tunnels are positioned proximal to the distal end 16b of the drive head 16, the suture-receiving channels 18a, 18b, 18c, 18d preferably also terminate at a position proximal to the distal end 16b of the head 16 to provide a channel-free portion 24 (shown in FIG. 1B) in the head 16. Moreover, where two suture tunnels are provided at different locations along the length of the drive head 16, a first pair of opposed suture-receiving channels, e.g., suture-receiving channels 18a, 18b, can have a length $L_1$ that is different than a length $L_2$ of a second pair of opposed suture-receiving channels, e.g., suture-receiving channels 18c, 18d, as shown in FIG. 1C.

The size and depth of each suture-receiving channel 18a, 18b, 18c, 18d can also vary, but they should be effective to seat a suture flush or sub-flush with the head 16 to allow the head 16 to be engaged by a driver tool without interference by the suture. In an exemplary embodiment, about 20% to 30%, and more preferably about 28%, of a cross-sectional surface area of the drive-head 16 is removed to form the suture-receiving channels 18a, 18b, 18c, 18d. As a result, the drive head 16, having suture-receiving channels 18a, 18b, 18c, 18d formed therein, will have a cross-sectional surface area at the proximal-most surface that represents about 72% of a nominal cross-sectional surface area within a perimeter of the drive head 16.

A person skilled in the art will appreciate that a variety of techniques can be used to attach a suture to an anchor, and that the anchor 10 is not limited to having one or more suture receiving tunnels and/or one or more suture-receiving channels.

Figure 2A:
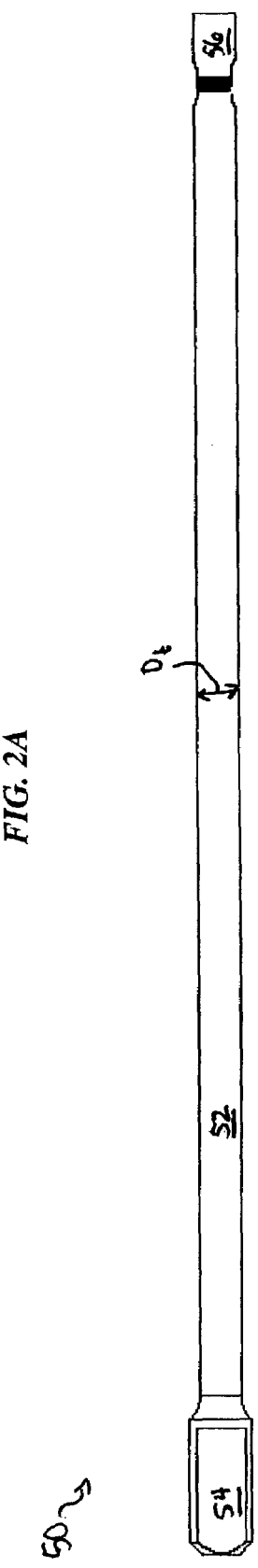
FIG. 2A is a side view of one embodiment of the driver tool in accordance with the present invention.
Figure 2B:
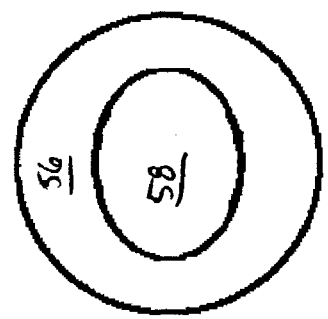
FIG. 2B is an end view of the distal-most end of the driver tool shown in FIG. 2A.

In use, the suture anchor 10 can be driven into bone using a driver tool, such as tool 50 shown in FIG. 2A. The driver tool 50 can have a variety of shapes and sizes, but preferably includes an elongate shaft 52 having a proximal, handle portion 54 and a distal end 56 having a socket 58 (FIG. 2B) formed therein and adapted to seat the head 16 of the suture anchor 10. The socket 58 of the driver tool 50, which is shown in FIG. 2B, has a substantially oval shape to fit around the oval-shaped head 16 of the anchor 10. The size of the socket 58 should be sufficient to provide a secure fit between the oval-shaped head 16 of the anchor 10 and the tool 50, and to prevent rotation of the tool 50 with respect to the anchor 10. The driver tool 50 also preferably includes an inner lumen (not shown) extending therethrough for receiving the remaining free ends of the suture(s) threaded through the head 16 of the anchor 10.

The suture anchor 10 can be used for a variety of medical procedures. In an exemplary embodiment, the suture anchor 10 is used in context of an arthroscopic shoulder repair, and more specifically, for attaching a detached labrum (as might result from a Bankart lesion or rotator cuff tear) to the glenoid rim of a scapula. It will be understood, however, that the system and method described herein are equally applicable to connecting detached tissue in other contexts as well. Further, the method described is merely exemplary of the steps involved in using any of the embodiments of the anchors of the present invention.

The procedure generally requires a delivery guide, e.g., a hollow guide tube, to be positioned at a desired implant site in the vicinity of a joint. A tap, or more preferably, an awl or a punch is then inserted through the tube and rotated until the depth mark reaches the cortical surface of the patient's bone. A length of suture is then threaded through each tunnel (only tunnel 26 is shown) in the head 16 of the anchor 10, and the remaining portion of the sutures are passed through the lumen in the driver tool. The free ends of the sutures extending out of the proximal end 54 of the driver tool 50 can optionally be pulled to hold the suture anchor 10 in the socket 58 of the driver tool 50. The anchor 10 can be then be inserted into bone by removing the tap from the delivery guide and introducing the drive tool with the anchor attached thereto through the delivery guide. The driver tool 50 is then twisted clockwise, applying a slight forward pressure, until the anchor 10 is at the desired depth. The driver tool 50 can then be removed by pulling straight back, which will expose the suture anchor and the sutures extending therefrom. The surgeon can then approximate the free end of detached labrum to the surface of the bone adjacent to the suture anchor, and the sutures can then be threaded through detached labrum and tied to secure the detached labrum to the bone.

Figure 3A:
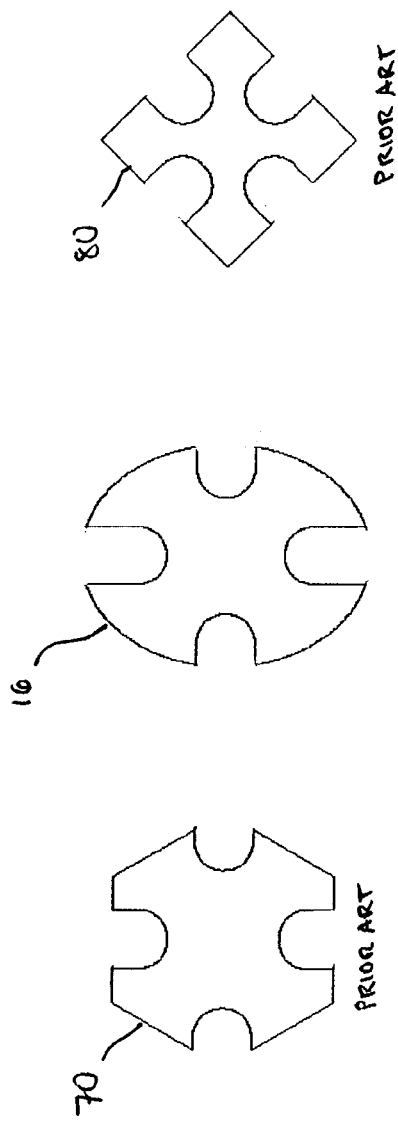
FIG. 3A is a top view illustration of the drive head of a suture anchor in accordance with the present invention compared to two prior art suture anchor drive heads.
Figure 3B:
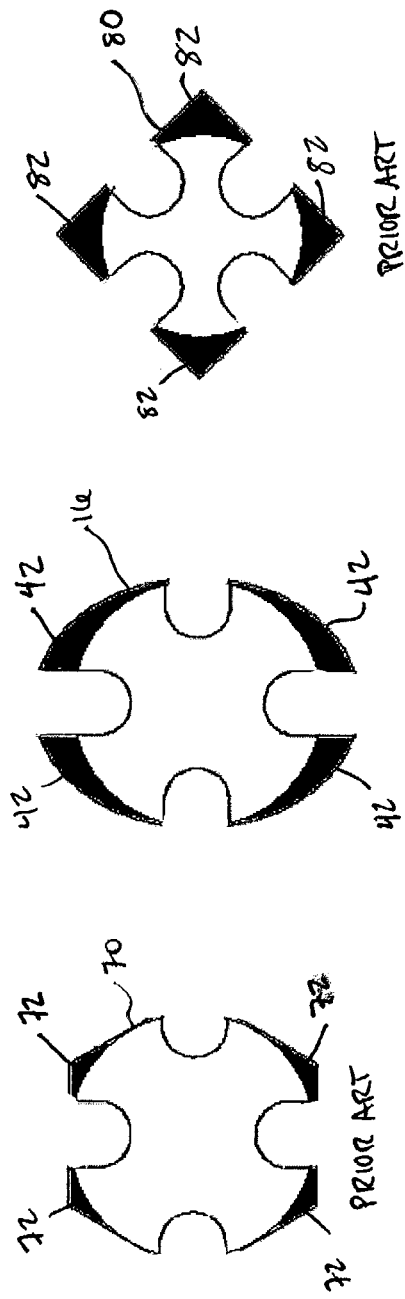
FIG. 3B is a top view illustration of the suture anchor drive heads shown in FIG. 3A having shaded areas illustrating the portion of the drive head that needs to be removed in order to strip the drive head.

FIGS. 3A and 3B illustrate the advantages of a suture anchor 10 according to the present invention compared to conventional, prior art suture anchor drive heads, such as the hexagonal-shaped head 70 and the square-shaped head 80 shown. Each anchor head 16, 70, 80 shown has a size that is adapted to fit within a driver tool having a socket having the same shape as the shape of the corresponding anchor head of the anchor to be driven into bone by the driver tool. The outside diameter of each corresponding driver tool however, is the same for all three anchor heads 16, 70, 80. During insertion of the anchor into bone, a torque is created by the driver tool 50. At some point, the torque created by the driver tool can cause the anchor head to strip, wherein portions of the outer surface of the head are removed thus allowing the head to rotate within the driver tool. FIG. 3B illustrates the portions 72, 42, 82 that would need to be removed in order for each of the illustrated anchor heads 70, 16, 80 to be stripped, e.g., to allow rotation of the anchor head within the socket in the driver tool. This is further indicative of the amount of material on the anchor head that interfaces with the driver. As shown, the portion 72 of the hexagonal-shaped anchor head that needs to be removed is less than the portion 42 of the anchor head 16 of the present invention that needs to be removed in order for the anchors to be stripped. The portion 82 of the square-shaped anchor head 80 that needs to be removed is more similar to the portion 42 on anchor head 16 that needs to be removed to result in stripping. However, the total cross-sectional area of the oval anchor head 16 is larger than the total cross-sectional area for the square head 80. As a result, the amount of material that interfaces with the driver on the oval head 16 is much larger than that for the square head 80. Thus, overall, the oval head has an increased stripping strength compared to the prior art anchor heads 70, 80.

The following table, which is based on each of the anchor heads 16, 70, 80 having dimensions such that each anchor head 16, 70, 80 is adapted to fit within a driver tool having the same outer diameter, further illustrates the differences between the prior art anchor heads 70, 80, and the anchor head 16 of the present invention:

TABLE 1

| Anchor Head | TOTAL CROSS-SECTIONAL SURFACE AREA | AREA OF MATERIAL THAT NEEDS TO BE REMOVED TO RESULT IN STRIPPING | PERCENT OF MATERIAL THAT NEEDS TO BE REMOVED TO RESULT IN STRIPPING |
| --- | --- | --- | --- |
| Hexagonal Anchor Head 70 | 0.0089 in$^2$ | 0.00073 in$^2$ | 8.2% |
| Oval Anchor Head 16 | 0.0105 in$^2$ | 0.00240 in$^2$ | 22.8% |
| Square Anchor Head 80 | 0.0060 in$^2$ | 0.00200 in$^2$ | 33.3% |

As shown in Table 1, since the anchor head 16 of the present invention requires more material to be removed to result in stripping of the head than the hexagonal anchor head 70, and since the anchor head 16 of the present invention has a much larger cross-sectional surface area compared to the square anchor head 80, the suture anchor 10 of the present invention will have a much higher stripping strength than the prior art anchors. In other words, the anchor head 16 of the present invention has a higher driver-to-anchor interface than the prior art anchors.

Figure 4:
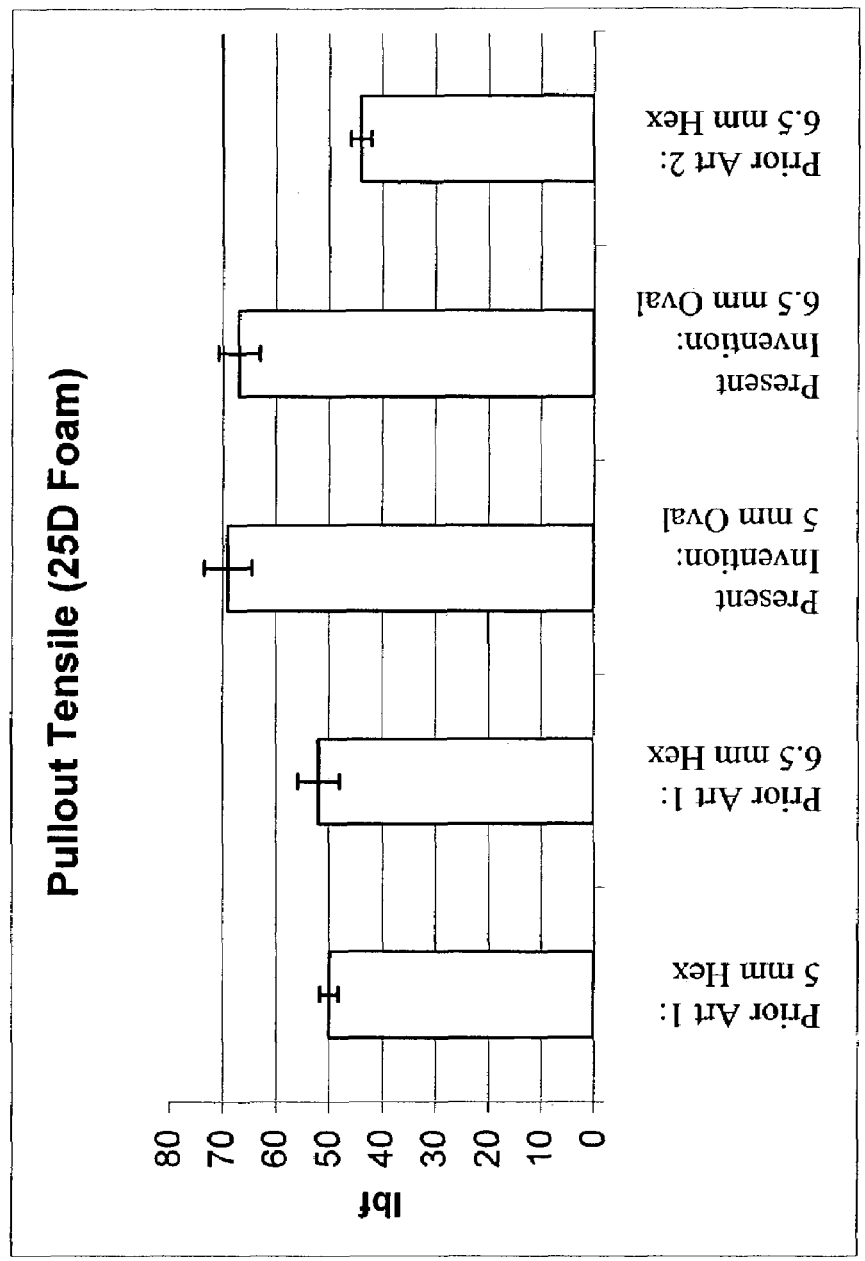
FIG. 4 is a chart illustrating the pullout tensile strength of several different suture anchors compared to a suture anchor in accordance with the present invention.
Figure 5:
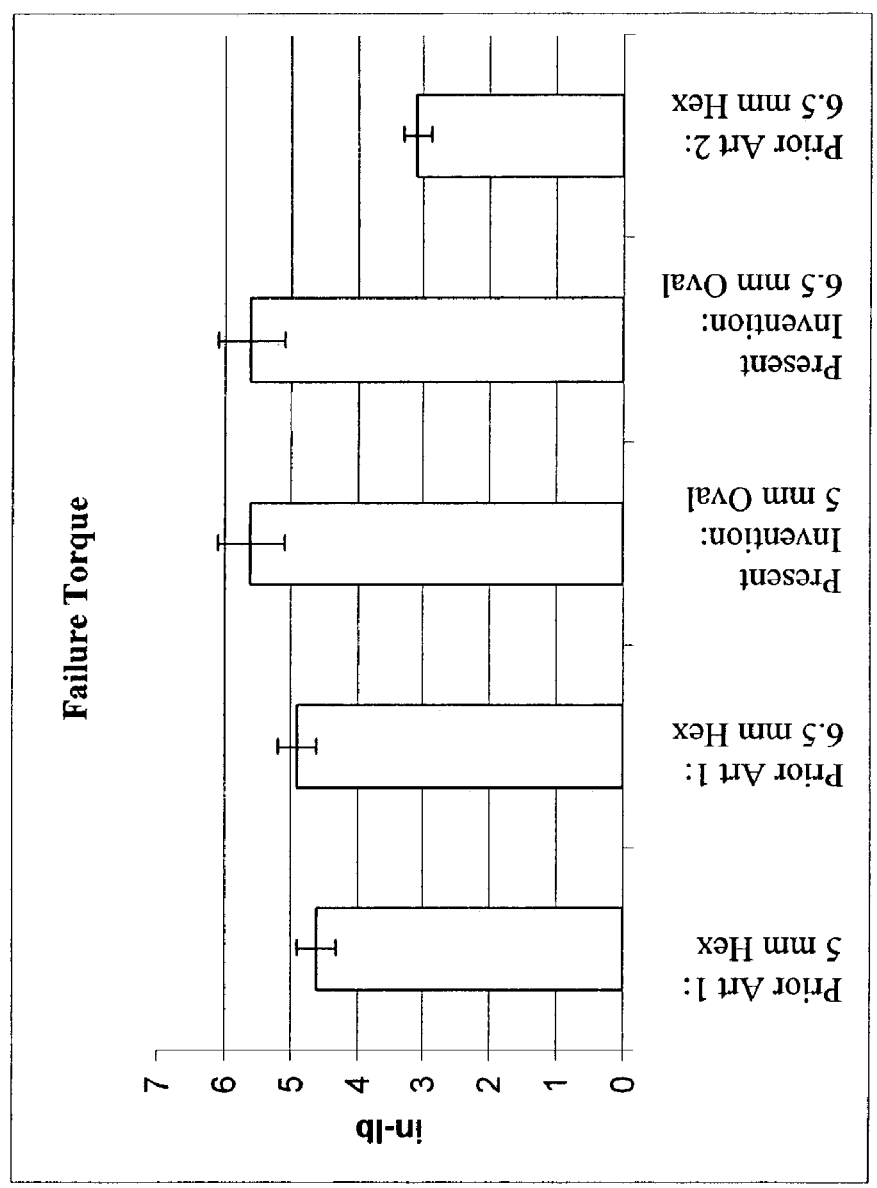
FIG. 5 is a chart illustrating the failure torque of several different suture anchors compared to a suture anchor in accordance with the present invention.

FIGS. 4 and 5 illustrate further advantages of the anchor 10 of the present invention over prior art anchors. The prior art anchors tested include the Prior Art 1: 5 mm Hex, the Prior Art 1: 6.5 mm Hex, and the Prior Art 2: 6.5 mm Hex. The Prior Art 1 anchor has a loop molded into and embedded within the anchor head to receive a length of suture, and the Prior Art 2 anchor has transverse suture-receiving bores formed therein.

The suture anchors of the present invention are referred to as the Present Invention: 5 mm Oval, and the Present Invention: 6.5 mm Oval. As shown in FIGS. 4 and 5, the anchors of the present invention have a pullout tensile, tested using 25D foam, and a failure torque that is greater than the pullout tensile and failure torque of the prior art anchors. Accordingly, the suture anchor 10 of the present invention shows a significant improvement over prior art anchors.

The suture anchor 10 of the present invention can be formed from a variety of materials, and can be formed from separate parts which are mated to one another. Preferably, however, the suture anchor 10 is formed as a single unit from a material that is suitable for human implantation, such as metal or plastic, and that is somewhat resilient. Exemplary materials include, for example, metals, metal alloys, absorbable polymers, such as, but not limited to, polylactic acid, polyglycolic acid, and copolymers thereof, non-absorbable polymers, such as, but not limited to, polyethylene, polypropylene, polyurethane, and acetal, and bioceramic materials, such as blends of polymers containing tricalcium phosphate, calcium sulfate, calcium carbonates, and hydroxy appatite.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A suture anchor, comprising:
   an elongate shank defining a longitudinal axis and having at least one bone-engaging thread formed thereon; and
   a drive head having a proximal end and a distal end mated to the elongate shank, the drive head having an oval shaped cross-section, at least one suture attachment member, and at least one longitudinally oriented suture receiving channel formed in a portion of the drive head such that a longest dimension of the suture receiving channel extends parallel to the longitudinal axis of the elongate shank.

2. The suture anchor of claim 1, wherein the suture attachment member comprises at least one suture tunnel extending transversely through the drive head.

3. The suture anchor of claim 2, wherein the at least one longitudinally oriented suture receiving channel is formed in an outer surface of the drive head and originates at and extends proximally from each opening of the at least one suture tunnel.

4. The suture anchor of claim 3, wherein the at least one suture tunnel is formed proximal to the distal end of the drive head to form a channel-free portion in the drive head.

5. The suture anchor of claim 3, wherein the suture-receiving channels are adapted to seat a suture flush or sub-flush with the outer surface of the drive head.

6. The suture anchor of claim 1, wherein the suture attachment member comprises a first, transversely oriented suture tunnel extending between a first pair of opposed, longitudinally oriented suture-receiving channels formed in an outer surface of the drive head, and a second transversely oriented suture tunnel extending between a second pair of opposed, longitudinally oriented suture-receiving channels formed in an outer surface of the drive head.

7. The suture anchor of claim 6, wherein the suture-receiving channels are adapted to seat a suture flush or sub-flush with the outer surface of the drive head.

8. The suture anchor of claim 6, wherein the drive head has a cross-sectional surface area at the proximal-most surface that represents about 72% of a nominal cross-sectional surface area within a perimeter of the drive head.

9. The suture anchor of claim 6, wherein the first and second suture tunnels are formed proximal to the distal end of the drive head to form a channel-free portion in the drive head.

10. The suture anchor of claim 1, wherein the drive head has a failure torque of at least about 5.0 inch pounds.

11. The suture anchor of claim 1, wherein the at least one bone-engaging thread comprises a helical thread.

12. The suture anchor of claim 1, wherein the elongate shank tapers from a proximal end to a distal end.

13. A suture anchor, comprising:
    an elongate shank defining a longitudinal axis and having at least one bone-engaging thread formed thereon; and
    a drive head having a proximal end and a distal end mated to the elongate shank, the drive head having an oval shaped cross-section, at least one suture attachment member, and at least one longitudinally oriented suture receiving channel formed in a portion of the drive head, wherein the suture attachment member comprises first and second suture tunnels extending transversely through the drive head, and wherein the first and second suture tunnels extend substantially perpendicular to each other.

14. The suture anchor of claim 13, wherein the first and second suture tunnels are formed proximal to the distal end of the drive head to form a channel-free portion in the drive head.

* * * * *